(12) United States Patent
Vanderlinde

(10) Patent No.: US 7,005,652 B1
(45) Date of Patent: Feb. 28, 2006

(54) SAMPLE-STAND FOR SCANNING ELECTRON MICROSCOPE

(75) Inventor: William Edward Vanderlinde, Columbia, MD (US)

(73) Assignee: The United States of America as represented by National Security Agency, Washington, DC (US)

( * ) Notice: Subject to any disclaimer, the term of this patent is extended or adjusted under 35 U.S.C. 154(b) by 0 days.

(21) Appl. No.: 10/962,872

(22) Filed: Oct. 4, 2004

(51) Int. Cl.
H01J 37/20 (2006.01)
H01J 37/28 (2006.01)
H01J 37/244 (2006.01)

(52) U.S. Cl. .................. 250/440.11; 250/310; 250/397
(58) Field of Classification Search ..................... None
See application file for complete search history.

(56) References Cited

U.S. PATENT DOCUMENTS

| | | | |
|---|---|---|---|
| 3,961,190 A * | 6/1976 | Lukianoff et al. | 250/310 |
| 4,308,457 A * | 12/1981 | Reimer | 250/397 |
| 4,596,929 A | 6/1986 | Coates et al. | |
| 4,627,009 A | 12/1986 | Holmes et al. | |
| 4,950,909 A | 8/1990 | Yokoto et al. | |
| 5,179,280 A | 1/1993 | Wang | |
| 5,412,210 A * | 5/1995 | Todokoro et al. | 250/310 |
| 5,510,624 A | 4/1996 | Zaluzec | |
| 5,717,206 A * | 2/1998 | Watanabe et al. | 250/310 |
| 6,025,592 A | 2/2000 | Knowles et al. | |
| 6,407,850 B1 | 6/2002 | Rojo et al. | |
| 6,777,678 B1 | 8/2004 | Vanderlinde | |

OTHER PUBLICATIONS

William E. Vanderlinde, "Forward Scattered Scanning Electron Microscopy for Semiconductor Metrology and Failure Analysis", Proceeedings from the 29th International Symposium for Testing and Failure Analysis, Nov. 2-6, 2003, Santa Clara, CA. USA.

* cited by examiner

Primary Examiner—Jack I. Berman
(74) Attorney, Agent, or Firm—Eric Froehlich

(57) ABSTRACT

The present invention is a sample-stage for a scanning electron microscope. The sample stage has a U-shaped base, horizontally oriented with the closed end forming the right side. A bottom member abuts the bottom of the U-shaped base, forming an interior cavity with the U-shaped base. An angled support member abuts the top of the U-shaped base farthest from the right side for holding a sample at a user-defined angle. A first reflector abuts a portion of the interior right side of the U-shaped base, and a second reflector abuts a portion of the top surface of the bottom member. A beam stop abuts a portion of the right side of the U-shaped base.

13 Claims, 5 Drawing Sheets

SAMPLE-STAND FOR SCANNING ELECTRON MICROSCOPE

FIELD OF THE INVENTION

The present invention relates, in general, to radiant energy, and in particular, to analyte supports.

BACKGROUND OF THE INVENTION

Optical techniques cannot be used to observe extremely fine features such as those on the surface of a semiconductor integrated circuit, because the wavelength of visible light is too large to distinguish such fine features. Therefore, particles in the form of an electron beam are used because an electron beam can be generated with a sufficiently small wavelength to distinguish such features.

Three types of electron beam microscopes have been developed: Transmission Electron Microscope (TEM), Scanning Transmission Electron Microscope (STEM), and Scanning Electron Microscope (SEM). Each of these microscopes operates by accelerating an electron beam toward the surface of an object to be viewed. To prevent an electric charge from accumulating on the surface, the object is often coated with a metal before being bombarded with an electron beam. When an electron beam strikes the surface of the object, secondary electrons are emitted from the object. The secondary electrons are collected by a detector, known as a secondary emission detector (SED). The detected secondary emission is then coordinated with the excitation signals applied to the electron beam to extract an image of the object.

The TEM, which is very expensive, generates an unmovable electron beam spot through a thin object of interest to produce an image of very high resolution. The STEM, which is also very expensive, generates an electron beam that is scanned through a thin object of interest to produce an image of very high resolution. The SEM, which is approximately ten times less expensive than either a TEM or a STEM, generates an electron beam that is scanned over a solid object of interest to produce an image of high resolution, but not as high as either a TEM or a STEM.

U.S. Pat. No. 4,596,929 entitled "THREE-STAGE SECONDARY EMISSION ELECTRON DETECTION IN ELECTRON MICROSCOPES," discloses a device that uses two grids to maximize the amount of secondary emission detected by a detector. The present invention does not employ two such grids. U.S. Pat. No. 4,596,929 is hereby incorporated by reference into the specification of the present invention.

U.S. Pat. No. 4,627,009 entitled "MICROSCOPE STAGE ASSEMBLY AND CONTROL SYSTEM," discloses a device for rotating and tilting a sample in a non-eucentric manner and compensate for the same so that an inspection point is within the field of view. The present invention does not rotate and tilt a sample in a non-eucentric manner and compensate for the same so that an inspection point is within the field of view. U.S. Pat. No. 4,627,009 is hereby incorporated by reference into the specification of the present invention.

U.S. Pat. No. 4,950,909 entitled "SAMPLE TILTING DEVICE IN ELECTRON MICROSCOPE," discloses a device for tilting a sample wherein no change in the field of view occurs when the sample is rotated conically about an axis. The present invention does not tilt and rotate a sample so that no change in the field of view occurs. U.S. Pat. No. 4,950,909 is hereby incorporated by reference into the specification of the present invention. U.S. Pat. No. 5,179,280, entitled "COMPUTER CONTROL OF THE ELECTRON MICROSCOPE SAMPLE STAGE," discloses a device for tilting a sample so that a plurality of different orientations are displayed stereoscopically with a spot representing a current orientation. The present invention does not tilt a sample so that a plurality of different orientations are displayed stereoscopically with a spot representing a current orientation. U.S. Pat. No. 5,179,280 is hereby incorporated by reference into the specification of the present invention.

U.S. Pat. No. 5,510,624, entitled "SIMULTANEOUS SPECIMEN AND STAGE CLEANING DEVICE FOR ANALYTICAL ELECTRON MICROSCOPE," discloses a device for cleaning a sample stage, a sample, and an interior of an analytical electron microscope. The present invention does not clean a sample stage, a sample, and an interior of an analytical electron microscope. U.S. Pat. No. 5,510,624 is hereby incorporated by reference into the specification of the present invention.

U.S. Pat. No. 6,025,592, entitled "HIGH TEMPERATURE SPECIMEN STAGE AND DETECTOR FOR AN ENVIRONMENTAL SCANNING ELECTRON MICROSCOPE," discloses a device that can heat a sample to 1500 degrees Celsius. The present invention does not heat a sample to 1500 degrees Celsius. U.S. Pat. No. 6,025,592 is hereby incorporated by reference into the specification of the present invention.

U.S. Pat. No. 6,407,850, entitled "AUTO TILT STAGE," discloses a device for tilting a sample stage of a TEM microscope to multiple positions. The present invention does not tilt a sample stage of a TEM microscope to multiple positions. U.S. Pat. No. 6,407,850 is hereby incorporated by reference into the specification of the present invention.

U.S. Pat. No. 6,777,678, entitled "SAMPLE-STAGE FOR SCANNING ELECTRON MICROSCOPE," discloses a device for measuring a sample with a SEM. A collimator and reflector are used to increase the image resolution of a horizontal sample imaged with a SEM to that of the STEM. The present invention does not image a horizontal image. U.S. Pat. No. 6,777,678 is hereby incorporated by reference into the specification of the present invention.

There exists a need to increase the resolution of images from a SEM without incurring the expense of either a STEM or a TEM, and without incurring the expense and inconvenience of creating a thin sample.

SUMMARY OF THE INVENTION

It is an object of the present invention to obtain an improved image on solid samples in a scanning electron microscope.

It is another object of the present invention to obtain the image resolution of a transmission electron microscope in a less expensive scanning electron microscope by using an angled sample holder and a two-stage reflector to obtain a perspective view of the sample. A perspective view allows details along the edge to be imaged. Furthermore, the high tilt angle causes as many as fifty percent of the high energy electrons to be forward scattered off the surface of the sample. These electrons carry high resolution and surface sensitive information.

The present invention is a sample-stage for obtaining the image resolution of a scanning transmission electron microscope in a less expensive scanning electron microscope.

The sample stage includes a U-shaped base, a bottom member, a support member, a first reflector, a second reflector, and a beam stop.

The U-shaped base is horizontally oriented with the closed end forming the right side. The U-shaped base has a right side, a top side, a bottom side, and a front side.

The bottom member has a top surface and abuts the bottom side of the U-shaped base, forming an interior cavity with the U-shaped base.

The support member has a left surface, a right surface, a front surface, a bottom, and a top. The bottom of the support member abuts the top of the U-shaped base farthest from the right side of the U-shaped base. The front surface of the support member nearest the bottom of the support member extends further to the right than the front surface of the support member nearest the top of the support member, forming a user-defined angle.

The first reflector, which abuts a portion of the interior right side of the U-shaped base, is a layer of user-definable atomic number material.

The second reflector, which abuts a portion of the top surface of the bottom member, is a layer of user-definable atomic number material.

The beam stop abuts a portion of the right side of the U-shaped base.

DETAILED DESCRIPTION

The present invention is a sample-stage for a scanning electron microscope (SEM) to improve the image resolution of the SEM to that of the more expensive transmission electron microscope (TEM). TEM's, which cost approximately ten times that of a SEM, capture higher resolution images than those captured by an unmodified SEM. The present invention is a sample-stage that can be used in a SEM to enable the SEM to capture images of solid samples with approximately the same resolution that a TEM has on thin samples. The present invention is particularly useful for imaging low atomic number materials such as photoresist and molecular semiconductors in their natural state, i.e. without sputter coating.

In a paper entitled "Forward Scattered Scanning Electron Microscopy for Semiconductor Metrology and Failure Analysis," William E. Vanderlinde published a paper describing the present invention and the results obtained imaging polysilicon, photoresist, and nanostructures as part of the Proceedings from the 29$^{th}$ International Symposium for Testing and Failure Analysis, published by the International Symposium for Testing and Failure Analysis.

Figure 1:
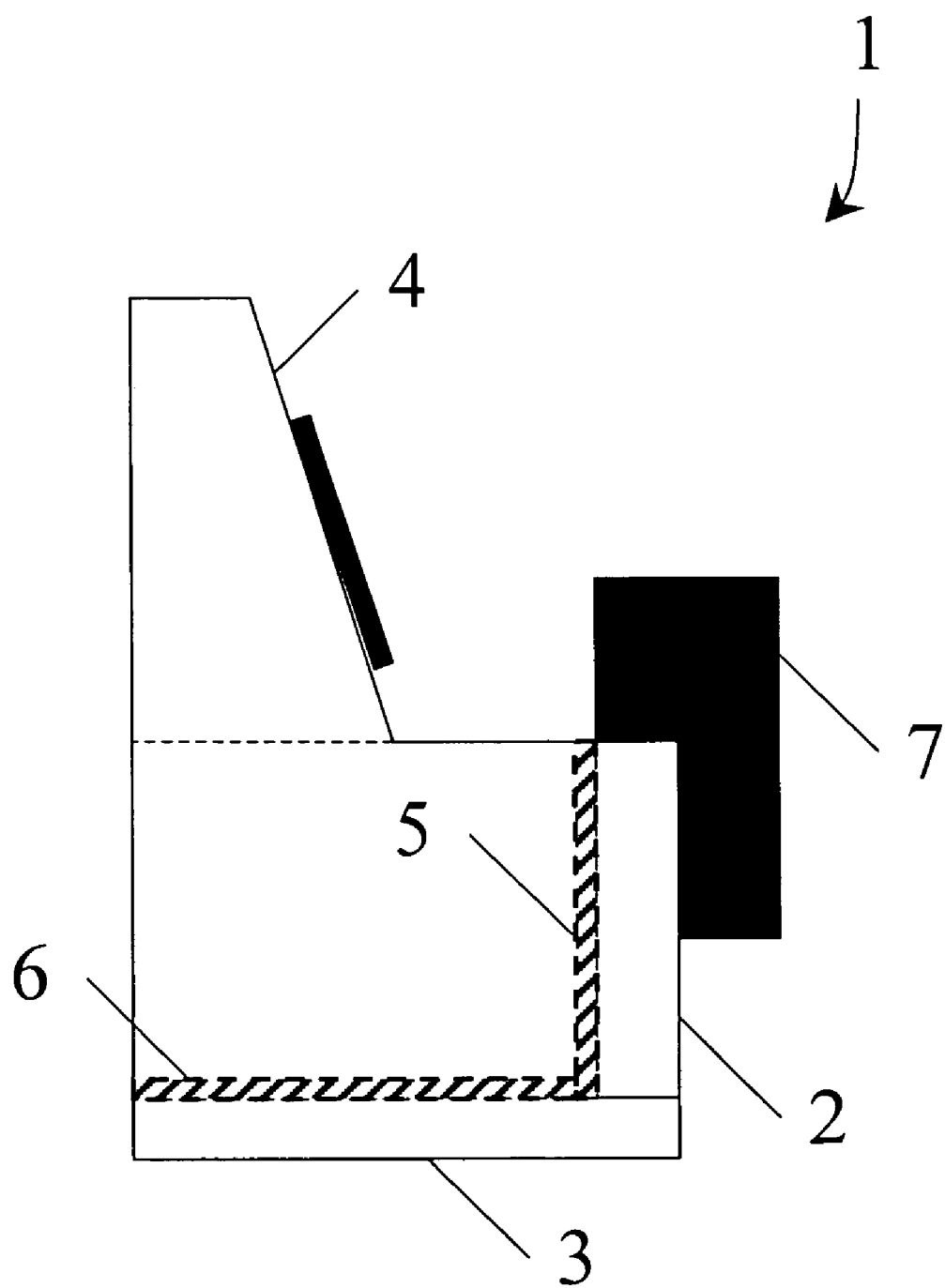
FIG. 1 is a side view of the present invention.

Referring to FIG. 1, a sample-stage 1 according to the present invention is shown. The sample-stage 1, which is to be used in a SEM (not shown), includes a U-shaped base 2, a bottom member 3, a support member 4, a first reflector 5, a second reflector 6, and a beam stop 7. The sample surface imaged with the present invention is pointed away from the detector of the SEM so that only forward scattered electrons produced from the primary incident electron beam contribute to the image. The first reflector 5 and second reflector 6 convert the forward scattered electrons to the lower energy secondary electrons typically collected by the detector of the SEM.

Figure 2:
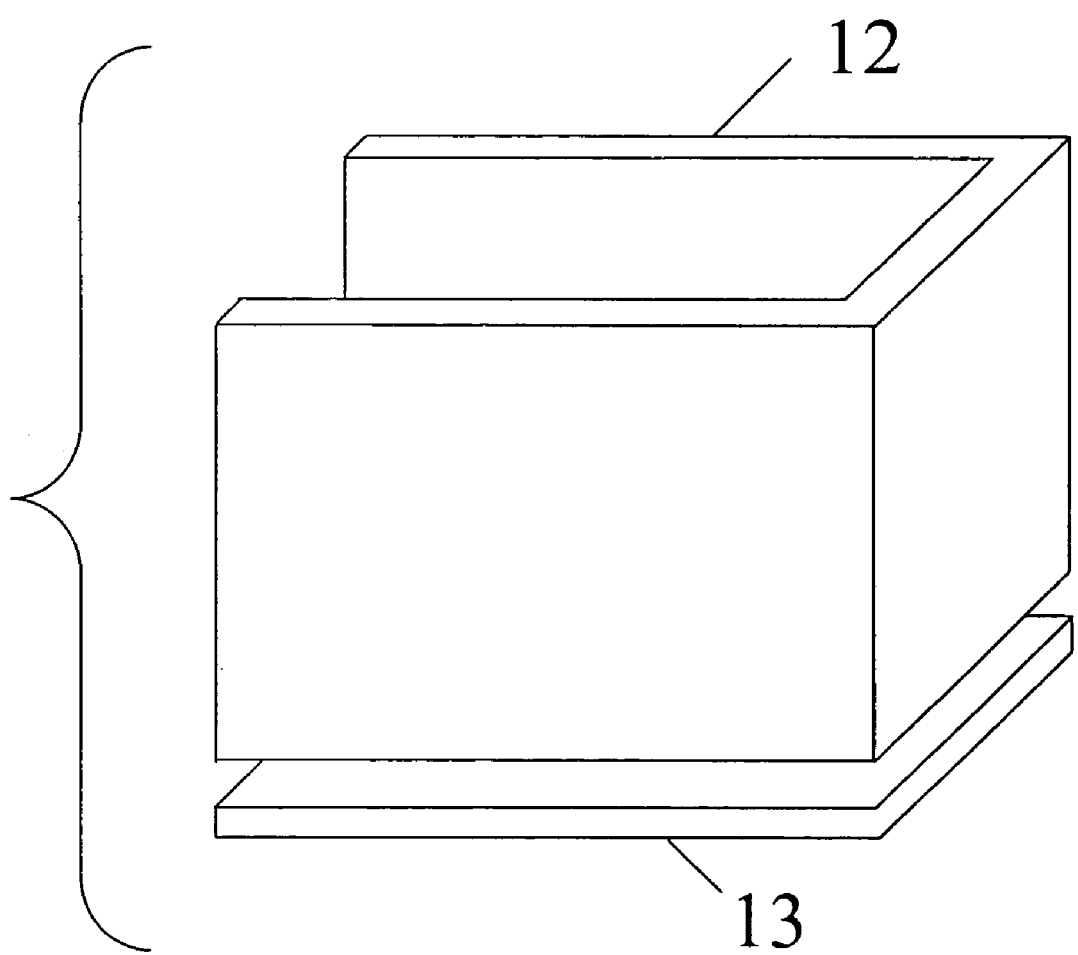
FIG. 2 is a perspective view of the U-shaped base and bottom member of the present invention.

Referring to FIG. 2, the U-shaped base 12 is oriented horizontally and has a right side, a top side, a bottom side, and a front side. The U-shaped base 12 has a user-definable length, height, width, and material. In the preferred embodiment, the U-shaped base 12 is 15 mm long, 10 mm high, 20 mm wide, and made of aluminum. In the preferred embodiment, a portion of the interior surface of the U-shaped base 12 is covered with carbon to absorb stray electrons.

The bottom member 13 has a top surface, and preferably has the same length and width dimensions of the U-shaped base 12. In the preferred embodiment, the bottom member 13 is made of aluminum. The top surface of the bottom member 13 abuts to the bottom side of the U-shaped base 12 forming an interior cavity. In the preferred embodiment, the portion of the bottom member 13 not covered by the U-shaped base 12 is covered with carbon to absorb stray electrons.

Figure 3:
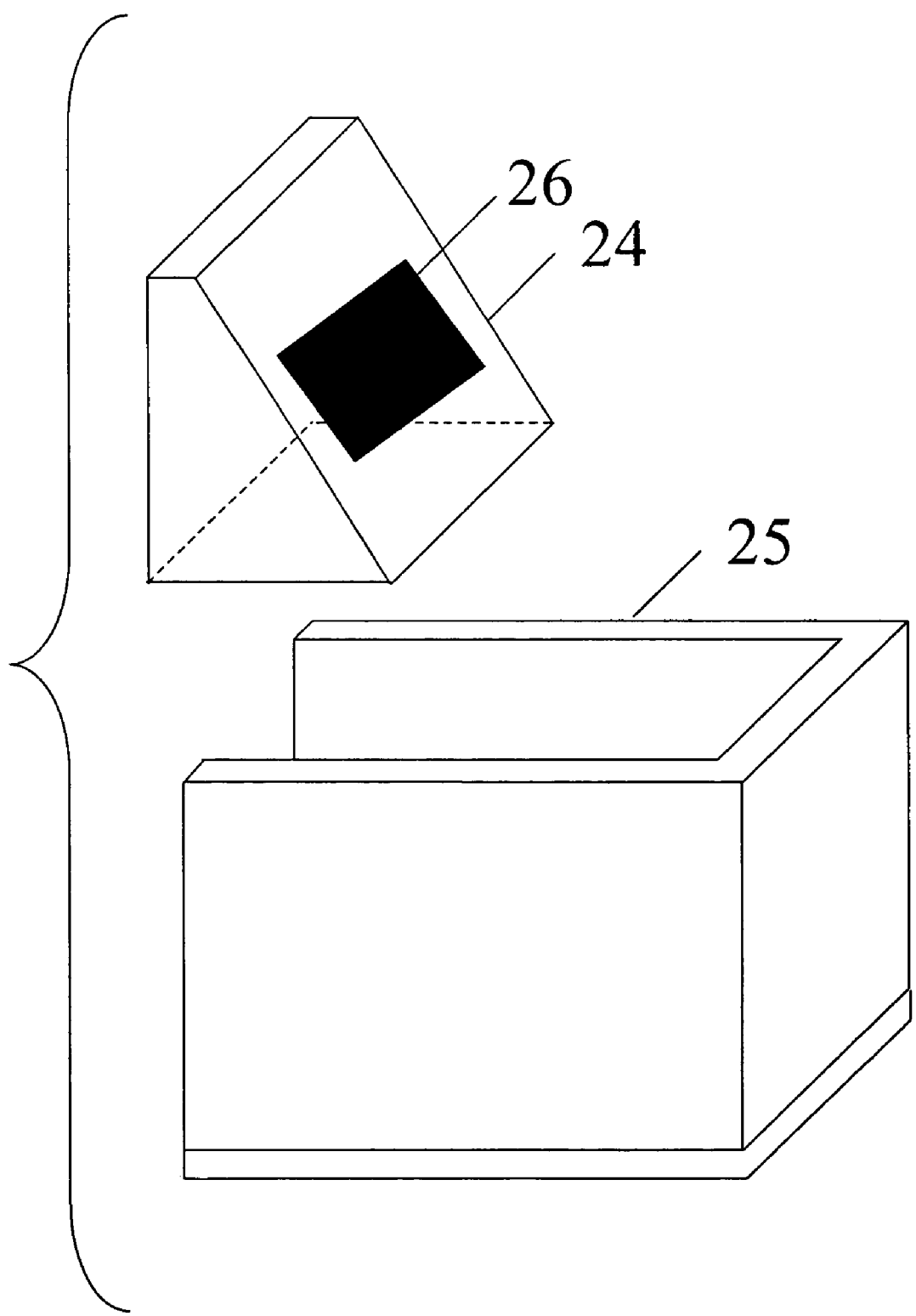
FIG. 3 is a perspective view of the U-shaped base, bottom member, and support member of the present invention.
Figure 4:
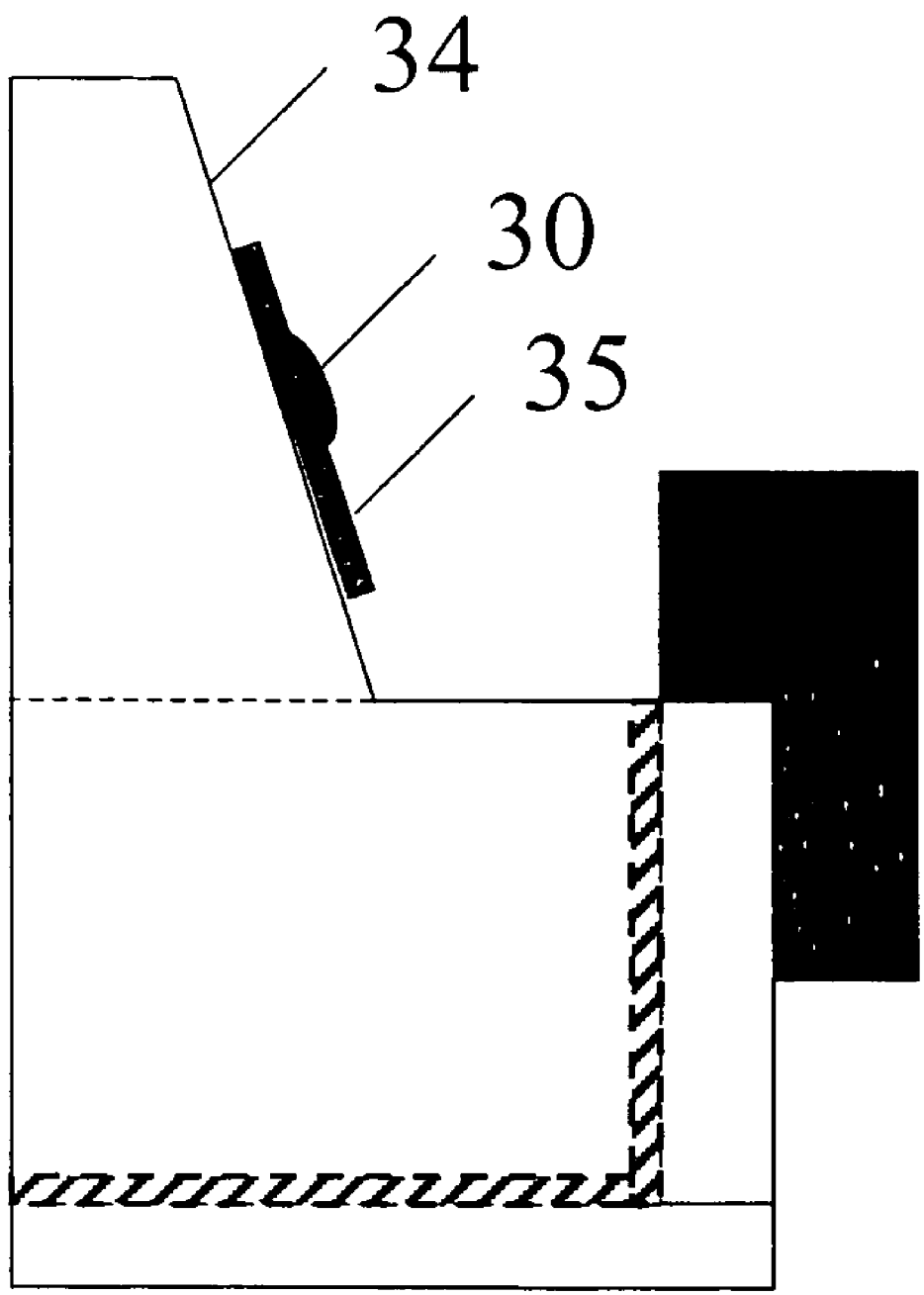
FIG. 4 is a side view of an alternate embodiment of the present invention.

Referring to FIG. 3, the support member 24 has a left surface, a right surface, a front surface, a bottom, and a top. The bottom of the support member 24 abuts the top of the U-shaped base 25 farthest from the right side of the U-shaped base 25. The bottom of the support member 24 extends further than the top of the support member so that the right surface is at a user definable angle as compared to the left surface. In the preferred embodiment, the user-definable angle of the support member 24 is 20 degrees from the vertical axis. Thus, a sample 26 in the preferred embodiment is tilted at 70 degrees from the horizontal axis. The support member 24 also has a user-definable length, height, width, and material. In the preferred embodiment, the support member 24 has a length of 5 mm measured at the top of the support member 4, a height of 10 mm, a width of 20 mm, and is made of aluminum. In the preferred embodiment, a portion of the support member 24 is covered with carbon to absorb stray electrons. In an alternate embodiment shown in FIG. 4, at least one sample retainer 30 is positioned on the support member 34 to releasably secure the sample 35 being imaged with the SEM. In the preferred embodiment, sample retainer 30 is a spring clip.

Referring again to FIG. 1, those persons skilled in the art will recognize that the U-shaped base 2, the bottom member 3, and the support member 4 may be made out of a single block of material.

The first reflector 5 depicted in FIG. 1 is placed on the interior right side of the U-shaped base 2 by abutting a user-definable atomic number material onto the right side of the U-shaped base 2. In the preferred embodiment, the first reflector 5 is a 1 micron thickness of an atomic number material, selected from the group of atomic number materials consisting of gold, tungsten, platinum, and lead on a silicon substrate. Each of the user-definable atomic number materials strongly reflects electrons from the electron beam 40 shown in FIG. 5.

Referring again to FIG. 1, the second reflector 6 is placed on a portion of the bottom member 3 not covered by the U-shaped base 2 by abutting a user-definable atomic number material onto the top surface of the bottom member 3. In the preferred embodiment, the second reflector 6 is a 1 micron thickness of an atomic number material, selected from the group of atomic number materials consisting of gold, tungsten, platinum, and lead on a silicon substrate. Each of the user-definable atomic number materials strongly reflects electrons from the electron beam 40 shown in FIG. 5.

Referring again to FIG. 1, a beam stop 7 abuts the right side of the U-shaped base 2. In the preferred embodiment, the beam stop 7 is made of graphite.

Figure 5:
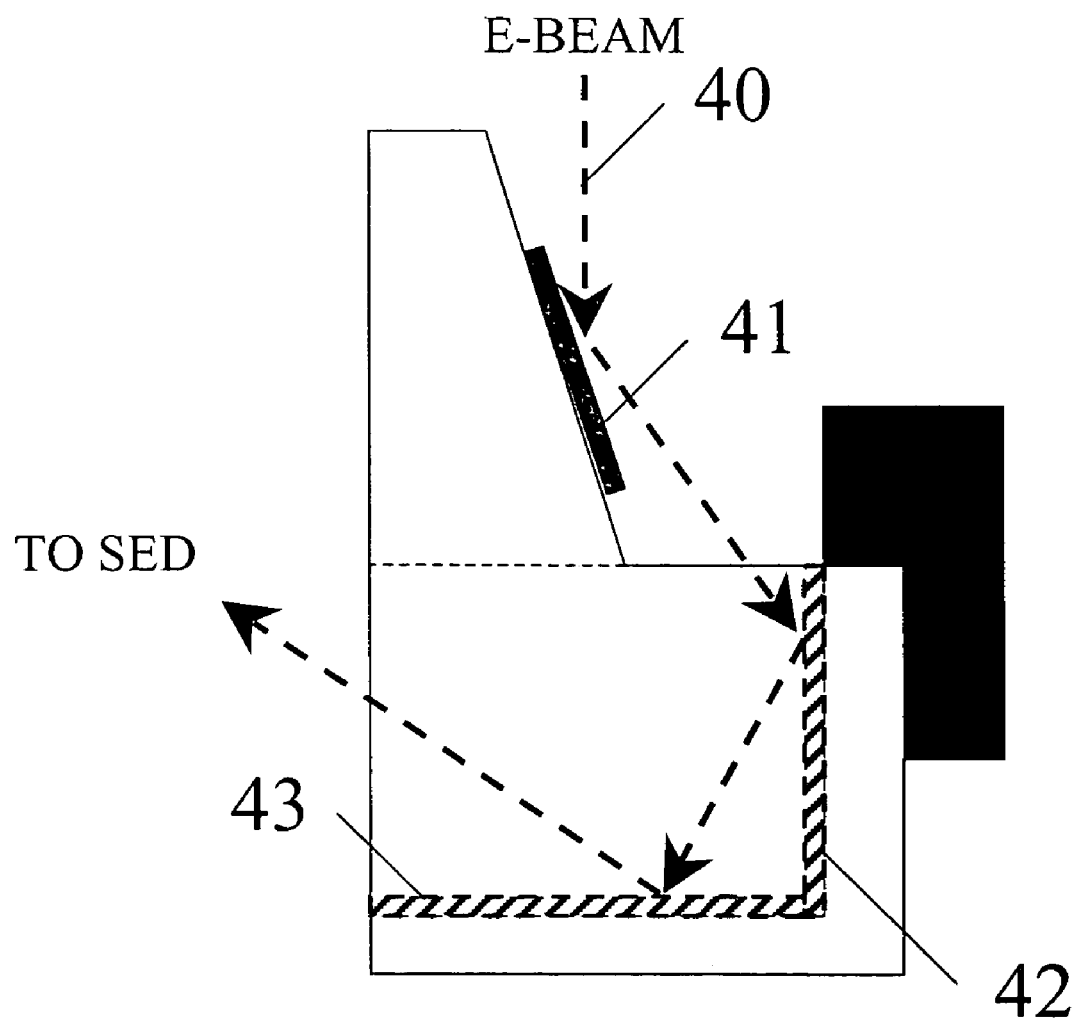
FIG. 5 is a side view of the present invention showing its operation.

As shown in FIG. 5, when imaging a sample 41, the high tilt angle causes forward scattered electrons of approximately the same energy level of the incident electron beam to strike the first reflector 42 and the second reflector 43. The first reflector 42 and the second reflector 43 form a two-stage reflector that strongly reflects electrons from the electron beam 40 that have scattered off the sample 41 to be imaged, and, therefore, cause lower energy secondary emission electrons to be directed toward the secondary emission detector (SED). Additional electrons received by the SED increases the resolution of the resulting image.

The high tilt angle of the present invention causes as many as fifty percent of the high energy incident electrons that impact the sample 41 to be scattered off the surface near the point of impact. These electrons carry very high resolution and surface sensitive information about the sample 41. The first reflector 42 and the second reflector 43 produce the secondary emission electrons collected by the secondary emissions detector of the SEM.

While the preferred embodiments of the invention have been illustrated and described, it will be apparent to those of ordinary skill in the art that various changes and modifications may be made without deviating from the inventive concepts set forth above.

What is claimed is:

1. A sample-stage for a scanning electron microscope, comprising:
    a) a U-shaped base, horizontally oriented, having a right side, a top side, a bottom side, and a front side;
    b) a bottom member, having a top surface, where the top surface of said bottom member abuts the bottom side of said U-shaped base, said bottom member forming an interior cavity within said U-shaped base;
    c) a support member, having a left surface, a right surface, a front surface, a bottom, and a top, where the bottom of the support member abuts the top side of said U-shaped base farthest from the right side of said U-shaped base, where the front surface of said support member nearest the bottom of said support member extends further than the front surface of said support member nearest the top of said support member so that the right surface of said support member is at a user-definable angle as compared to the left surface of the support member;
    d) a first reflector abutting the right side and within the interior cavity of said U-shaped base, where the first reflector is a user-definable atomic number material;
    e) a second reflector abutting the top surface of the bottom member within the interior cavity of said U-shaped base, where the first reflector is a user-definable atomic number material; and
    f) a beam stop, abutting a portion of the right side of said U-shaped base.

2. The device of claim 1, wherein the front side and the right side of said U-shaped base are 15 mm in length and a right side 20 mm in length, respectively.

3. The device of claim 2, wherein said U-shaped base is comprised of aluminum.

4. The device of claim 3, wherein the front surface and the left side of said support member are 15 mm in length and 20 mm in length, respectively.

5. The device of claim 4, wherein said support member is comprised of aluminum.

6. The device of claim 5, wherein said first reflector and said second reflector are each comprised of:
    a) a silicon substrate; and
    b) a user-defined atomic number material selected from the group of user-defined atomic number materials consisting of gold, tungsten, platinum, lead, and any combination thereof, deposited onto the silicon substrate.

7. The device of claim 6, wherein the user-definable angle of the right surface of said support member is 20 degrees from a vertical axis.

8. The device of claim 7, further comprising at least one sample retainer.

9. The device of claim 8, wherein said at least one sample retainer is comprised of a spring clip.

10. The device of claim 1, wherein said first reflector and said second reflector are each comprised of:
    a) a silicon substrate; and
    b) a user-defined atomic number material selected from the group of user-defined atomic number materials consisting of gold, tungsten, platinum, lead, and any combination thereof, deposited onto the silicon substrate.

11. The device of claim 1, wherein the user-definable angle of the right surface of said support member is 20 degrees from a vertical axis.

12. The device of claim 1, further comprising at least one sample retainer.

13. The device of claim 12, wherein said at least one sample retainer is comprised of a spring clip.

* * * * *